(12) United States Patent
Tanaka et al.

(10) Patent No.: US 9,315,562 B2
(45) Date of Patent: Apr. 19, 2016

(54) HIGH-STRENGTH COLLAGEN FIBER MEMBRANE AND A MANUFACTURING METHOD THEREOF

(75) Inventors: Junzo Tanaka, Tokyo (JP); Toshiyuki Ikoma, Tokyo (JP); Tomohiko Yoshioka, Tokyo (JP)

(73) Assignee: Tokyo Institute of Technology, Tokyo (JP)

(*) Notice: Subject to any disclaimer, the term of this patent is extended or adjusted under 35 U.S.C. 154(b) by 206 days.

(21) Appl. No.: 13/989,397

(22) PCT Filed: Nov. 28, 2011

(86) PCT No.: PCT/JP2011/077424
§ 371 (c)(1),
(2), (4) Date: Jul. 8, 2013

(87) PCT Pub. No.: WO2012/070679
PCT Pub. Date: May 31, 2012

(65) Prior Publication Data
US 2014/0044948 A1   Feb. 13, 2014

(30) Foreign Application Priority Data
Nov. 26, 2010   (JP) ................................. 2010-264375

(51) Int. Cl.
*C07K 14/78*   (2006.01)
*A61L 15/32*   (2006.01)
(Continued)

(52) U.S. Cl.
CPC ............... *C07K 14/78* (2013.01); *A61L 15/325* (2013.01); *A61L 27/24* (2013.01); *A61L 27/3604* (2013.01); *A61L 31/044* (2013.01); *C12N 5/0068* (2013.01); *C12N 2533/54* (2013.01)

(58) Field of Classification Search
None
See application file for complete search history.

(56) References Cited

U.S. PATENT DOCUMENTS 5,206,028 A * 4/1993 Li ................................. 424/484
6,391,333 B1 * 5/2002 Li et al. ........................ 424/443
(Continued)

FOREIGN PATENT DOCUMENTS

JP   08-228768   9/1996
JP   2006-257014 A   9/2006
(Continued)

OTHER PUBLICATIONS

Ikoma, T.; Yunoki, S.; Tanaka, J.; "Collagen Derived from Scale and Method for Obtaining the Same Collagen". [JP 2006-257014]; Sep. 28 2006; (EPO—Machine Translation (English)).*
(Continued)

*Primary Examiner* — David Sample
*Assistant Examiner* — Donald M Flores, Jr.
(74) *Attorney, Agent, or Firm* — Kilpatrick, Townsend & Stockton LLP

(57) ABSTRACT

The object of the present invention is to provide a collagen fiber membrane, which has sufficient strength and can be used as a cell culture substrate, a scaffold material for regenerative medicine (for example, material for tissue engineering of cartilage, bone, ligament, corneal stroma, skin, or liver), an implantation material (for example, wound dressing material, bone grafting material, hemostatic material, anti-adhesive material) or a carrier for drug delivery. The object of the present invention can be solved by a fish-derived collagen fiber membrane, characterized in that (1) a tensile strength is 30 MPa or more, (2) a density determined by the gravimetric method, is 0.4 g/cm³ or more, and (3) an average membrane thickness is 1 μm to 2 mm, and a variation in membrane thickness is plus or minus 30%, relative to the average membrane thickness.

12 Claims, 7 Drawing Sheets

(51) Int. Cl.
 *A61L 27/24* (2006.01)
 *A61L 27/36* (2006.01)
 *A61L 31/04* (2006.01)
 *C12N 5/00* (2006.01)

(56) References Cited

U.S. PATENT DOCUMENTS

| | | | |
|---|---|---|---|
| 6,541,023 | B1 | 4/2003 | Andre et al. |
| 2006/0029639 | A1 | 2/2006 | Kamimura et al. |
| 2006/0210601 | A1 | 9/2006 | Nagai et al. |
| 2009/0069540 | A1* | 3/2009 | Yunoki et al. .............. 530/356 |
| 2010/0090924 | A1 | 4/2010 | Honda et al. |
| 2013/0337227 | A1* | 12/2013 | Tanaka et al. .............. 428/141 |

FOREIGN PATENT DOCUMENTS

| | | | | |
|---|---|---|---|---|
| JP | 2006257014 A | * | 9/2006 | ............ C07K 14/78 |
| WO | 2005/014774 A1 | | 2/2005 | |
| WO | 2005/053617 A2 | | 6/2005 | |

OTHER PUBLICATIONS

Matsuda, A. et al., "Biofunctional materials: utilization of presents from the sea," Materials Integration, 20(5):11-16, 2007.

Takezawa, T. et al., "Collagen vitrigel membrane useful for paracrine assays in vitro and drug delivery systems in vivo," Journal of Biotechnology, 131:76-83, 2007.

Takezawa, T. et al., "Development of novel cell culture systems utilizing the advantages of collagen vitrigel membrane," Yakugaku Zasshi, 130(4):565-574, 2010.

Xu, Z. et al., "Kakyo Mitsudo no Kotonaru Sakana Uroko Collagen Sen' imaku no Kikaiteki Tokusei," The 33rd Annual Meeting of the Japanese Society for Biomaterials Yokoshu, Nov. 21, 2011, p. 108.

Chen et al., "Microstructures and rheological properties of tilapia fish-scale collagen hydrogels with aligned fibrils fabricated under magnetic fields," Acta Biomaterialia, 2011 (Epubl Sep. 2010), vol. 7(2), pp. 644-652.

Snakar et al., "Preparation and partial characterization of collagen sheet from fish (*Lates calcarifer*) scales," International Journal of Biological Macromolecules, 2008 (Epub 2007), vol. 42(1), pp. 6-9.

Wang et al., "Collagen fibres with improved strength for the repair of soft tissue injuries," Biomaterials, 1994, vol. 15(7), pp. 507-512.

European Supplementary Search Report, Oct. 14, 2010, EP Application No. 11 84 3962.9, 6 pages.

\* cited by examiner (A)

(B)

(A)

(B)

(C)

HIGH-STRENGTH COLLAGEN FIBER MEMBRANE AND A MANUFACTURING METHOD THEREOF

CROSS-REFERENCE TO RELATED APPLICATIONS

This application is a national phase application under 35 U.S.C. 371 claiming priority to PCT/JP2011/077424, filed Nov. 28, 2011, which application claims priority to JP 2010-264375, filed Nov. 26, 2010, the teachings of which are hereby incorporated by reference in their entireties for all purposes.

TECHNICAL FIELD

The present invention relates to a high-strength collagen fiber membrane and a manufacturing method thereof. The high-strength collagen fiber membrane of the present invention can be used effectively as a cell culture substrate, a scaffold material for regenerative medicine, an implantation material and a carrier for drug delivery.

BACKGROUND ART

Collagen is an important protein that contributes 30% of all proteins in a living body and functions as a support for bone and cell adherence. For example, collagen is a main constituent element of tissues, such as bone, cartilage, ligament, tendon, corneal stroma, skin, liver, muscle, and the like of the human body. Thus, the collagen material is useful as biomaterials, such as a cell culture substrate, a scaffold material for regenerative medicine (material for tissue engineering of cartilage, bone, ligament, corneal stroma, skin, or liver, for example), an implantation material (wound dressing material, bone grafting material, hemostatic material, or anti-adhesive material, for example) or a carrier for drug delivery. In particular, the collagen material is absolutely imperative for huge tissue regeneration by regenerative medicine. However, a mechanical characteristic of collagen material is not satisfactory and thus, a clinical use thereof is limited.

Hitherto, the following materials are reported as materials obtained by a fibril formation from soluble collagen in vitro. For example, Patent Reference 1 discloses a collagen membrane obtained by forming collagen fibrils from fishskin-derived collagen, freeze drying the obtained collagen gel containing the collagen fiber, and then cross-linking the freeze-dried gel with thermal cross-linking or chemical cross-linking (using a solution of carbodiimide, glutaraldehyde, succinimide or the like). Further, Patent Reference 2 discloses a stretchable collagen material obtained in a solution by forming collagen fibrils from fishskin-derived collagen and chemically cross-linking collagen fibers with a cross-linker, simultaneously.

However, the above materials are porous, and thus, do not have sufficient strength (mechanical characteristic) even after the collagen is cross-linked.

Non-Patent Reference 1 and Non-Patent Reference 2 disclose that a collagen-thin membrane containing collagen fiber is obtained by using a bovine-derived collagen. The collagen-thin membrane has a certain level of strength due to vitrification (drying for at least two weeks), although the collagen-thin membrane is not cross-linked. However, the strength of the collagen-thin membrane is not still sufficient. Therefore, the collagen-thin membrane, wherein the outer edge thereof is reinforced by nylon frame, is only commercially available as a cell culture substrate (Non-Patent Reference 1 and Non-Patent Reference 2).

CITATION LIST

Patent Literature

[Patent Reference 1] Japanese Translation Publication (Kohyo) No. 2003-534858
[Patent Reference 2] Japanese Unexamined Patent Publication (Kokai) No. 2005-334625
[Patent Reference 3] Japanese Unexamined Patent Publication (Kokai) No. 8-228768
[Patent literature 4] Japanese Application No. 2005-513025

Non-Patent Literature

[NON-PATENT Reference 1] YAKUGAKU ZASSHI (Japan) 2010, vol. 130, p. 565-574
[NON-PATENT Reference 2] Journal of BIOTECHNOLOGY (Germany) 2007, vol. 131, p. 76-83

SUMMARY OF INVENTION

Technical Problem

The object of the present invention is to provide a collagen fiber membrane which has a sufficient strength and can be used as a cell culture substrate, a scaffold material for regenerative medicine (for example, material for tissue engineering of cartilage, bone, ligament, coreal stroma, skin, or liver), an implantation material (for example, wound dressing material, bone grafting material, hemostatic material, anti-adhesive material) or a carrier for drug delivery.

Solution to Problem

Under appropriate salt concentration and pH conditions, it is known that collagen fibril is formed. Further, as a method for condensing collagen fibers, for example, a method for condensation by a centrifugation, or a method for dehydrating collagen hydrogel in an atmosphere of dry air, is disclosed (Non-Patent Reference 3 and Non-Patent Reference 4). However, in these methods, achieving an even thickness of the collagen fiber membrane is quite difficult.

The present inventors have conducted intensive studies into collagen fiber membranes having sufficient strength as the cell culture substrates, the scaffold materials for regenerative medicine, or the implantation materials. As a result, the present inventors found that a fish (particularly fish scale)-derived collagen fiber membrane, which is obtained by a method of desalination through the use of a graded series of purified water and lower alcohol and evaporating a solvent from only a side of the collagen fiber gel, has an even thickness, and thereby a density of the collagen fiber membrane is increased, and further a strength thereof can be surprisingly increased. In particular, as the fish-derived collagen fiber membrane is treated by the graded series of purified water and ethanol before drying, a residual salt therein can be lowered greatly. That is to say, the inventors found that the collagen fiber membrane with high density and high strength can be prepared by covering a lower surface and an upper surface of the collagen fiber gel and evaporating a solvent only from a side of the collagen fiber gel. Further, it is necessary, in the method for the fish-derived collagen fiber membrane preparation, to decrease thickness variations in a membrane, in order to increase the fish-derived collagen fiber membrane's strength. Furthermore, a chemical cross-linking treatment by a vapor method in low pressure to a dried collagen fiber membrane makes it possible to obtain the fish-derived collagen membrane in which the strength thereof is further increased.

The present invention is based on the above findings.

Thus, the present invention relates to a fish-derived collagen fiber membrane, characterized in that (1) a tensile strength is 30 MPa or more, (2) a density determined by the gravimetric method, is 0.4 g/cm$^3$ or more, and (3) an average membrane thickness is 1 μm to 2 mm, and a variation in membrane thickness is plus or minus 30%, relative to the average membrane thickness.

According to a preferable embodiment of the fish-derived collagen fiber membrane, the collagen is derived from a fish scale.

Further, according to another preferable embodiment of the fish-derived collagen fiber membrane, the collagen fiber membrane is cross-linked.

According to another preferable embodiment of the fish-derived collagen fiber membrane, a degree of cross-linking is 5% or more (determined by quantifying a free amino group).

According to another preferable embodiment of the fish-derived collagen fiber membrane, a denaturation temperature of collagen is higher than a denaturation temperature of collagen before fibril formation by 5° C. or more. Further, according to a preferable embodiment of the cross-linked, fish-derived collagen fiber membrane, a denaturation temperature of collagen is higher than a denaturation temperature of collagen before fibril formation by 10° C. or more.

Further, according to another preferable embodiment of the cross-linked, fish-derived collagen fiber membrane, a swelling ratio thereof is 300% or less.

Furthermore, according to a preferable embodiment of the fish-derived collagen fiber membrane, the collagen fiber membrane exhibits an inducibility of osteoblast differentiation.

Further, the present invention relates to a method for preparing a fish-derived collagen fiber membrane, comprising the steps of: (1) forming a collagen fibril from a soluble collagen in a collagen solution, to obtain a collagen fiber gel of 0.3% by weight or more, (2) removing a salt from the collagen fiber gel using a graded series of purified water and ethanol, and (3) drying the collagen fiber gel by covering a lower surface and an upper surface of the collagen fiber gel and removing a solvent from a side of the collagen fiber gel.

Further, according to a preferable embodiment of the method for preparing a fish-derived collagen fiber membrane, the collagen is derived from a fish scale.

Further, according to a preferable embodiment of the method for preparing a fish-derived collagen fiber membrane, the method comprises a step of cross-linking the fish-derived collagen fiber membrane.

Advantageous Effects of Invention

The high-strength collagen fiber membrane of the present invention is a high-density collagen fiber membrane which has not existed until now. Further, the variation of membrane thickness is low, and thus, there is no lower-strength region in the collagen fiber membrane. Thus, the collagen fiber membrane of the present invention can exhibit high tensile strength. The collagen fiber membrane having such a high mechanical strength of the present invention is useful as a cell culture substrate, a scaffold material for regenerative medicine, an implantation material, or a carrier for drug delivery. Therefore, said invention can solve a problem related to a handling in medical practice caused by a lack of mechanical strength thereof.

Furthermore, the high-strength collagen fiber membrane of the present invention is prepared using collagen derived from fish which hardly has zoonosis, and therefore, can be safely used as scaffold material for regenerative medicine, or implantation material, compared to a collagen material prepared using collagens derived from bovine that have bovine spongiform encephalopathy (BSE), swine that have foot-and-mouth disease, or birds that have influenza infection.

BRIEF DESCRIPTION OF THE DRAWINGS

FIG. 10 is a set of paragraphs showing shapes of human bone-marrow-derived mesenchymal stem cells in culture on:

the collagen fiber membrane (A), a collagen transparent membrane (B), or a polystyrene plate (C).

Figure 11:
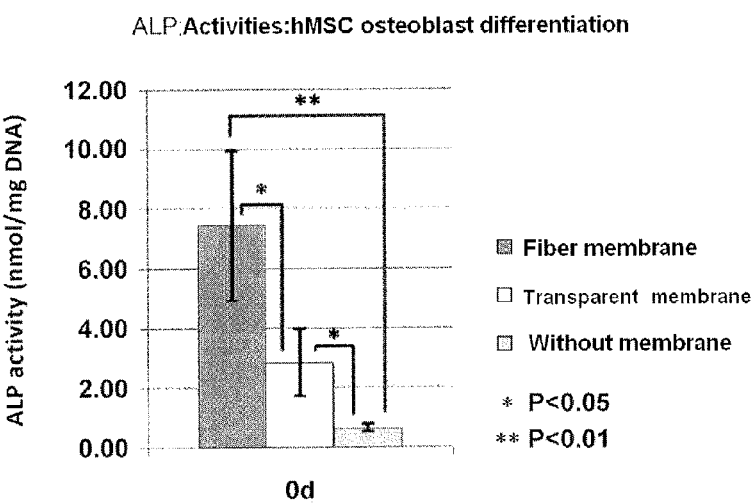

FIG. 11 is a graph showing alkaline phosphatase activities of human bone-marrow-derived mesenchymal stem cells cultured for 24 hours on the collagen fiber membrane, the collagen transparent membrane, or the polystyrene plate.

DESCRIPTION OF EMBODIMENTS

[1] Fish-Derived Collagen Fiber Membrane

The fish-derived collagen fiber membrane of the present invention has (1) a tensile strength at 30 MPa or more, (2) a density determined by the gravimetric method at 0.4 g/cm$^3$ or more, and (3) an average membrane thickness of 1 μm to 2 mm. Further, a variation in membrane thickness thereof is plus or minus 30% relative to the average membrane thickness.
(Fish-Derived Collagen)

A fish-derived collagen contained in the fish-derived collagen fiber membrane of the present invention is not particularly limited, so long as it is type I collagen derived from fish, but is preferably a collagen derived from fish scale. This is because the collagen derived from fish scale may easily form collagen fibrils and has an extremely fast rate of collagen fibril formation, in comparison with other collagens. Further, an interaction between collagen fibers is strong in the collagen fiber membrane obtained from fish scale-derived collagen, and thus, the collagen fiber membrane has an especially strong mechanical strength. As for the fish used to obtain the fish-derived collagen, there may be mentioned tilapia, salt-water venomous catfish, labeo rohita, catla, carp, channa argus, pirarucu, sea bream, bastard halibut, shark, salmon, and the like. However, fish which live in rivers, lakes, or seas with warm water temperatures is preferable, in view of an after-mentioned denaturation temperature. In particular, examples of such fish include fish belonging to the *Oreochromis* genus, and tilapia in particular is preferable. The collagen obtained from fish of the *Oreochromis* genus has a relatively-high denaturation temperature. For example, *Oreochromis niloticus*, farmed in Japan or China, is easily available, and thus a large amount of collagen can be obtained therefrom.

Type I collagen derived from fish scale, which forms a "triple-helix structure (tropocollagen)" by assembling three polypeptide chains with a molecular weight of approximately 100 kD per polypeptide chain, has a molecular weight of approximately 300 kD. The fish scale-derived type I collagen has a stiff rod-like shape with a length of 300 nm and a diameter of 1.5 nm. The specific "triple-helix structure (tropocollagen)" of type I collagen derived from fish is due to an amid acids sequence of the polypeptide chain. The polypeptide chain comprises repeats of a unit of three amino acids i.e. "G-X-Y". The "G" is glycin, many of "X" are proline, and many of "Y" are hydroxyproline. Hydroxyproline is not contained in common proteins, but contained specifically in collagen. It is considered that a triple-helix structure of collagen becomes stabilized by hydrogen bonds between the hydroxyl group of hydroxyproline and hydration water. Collagen is polyamphoteric molecules with amino groups and carboxyl groups. That is, collagen charges positively in acidic solutions, and charges negatively in alkaline solutions. Further, collagen outwardly charges neutral in or around neutral pH. The collagen molecule having a triple-helix structure (tropocollagen) forms collagen microfibril in or around neutral pH, although collagen fibril formation is strongly dependent on salt types and temperature.

When the temperature is raised, the "triple-helix structure" of collagen consisting of three polypeptides untwists, and then three polypeptides come to pieces. Consequently, the collagen changes into a gelatin. Change from collagen to gelatin is referred to as denaturation. Once the denaturation of collagen occurs, it is difficult to restore the gelatin to the "triple-helix structure" even if the temperature is lowered. At best, a denaturation temperature of collagen derived from a certain living being is slightly higher than a temperature of habitat environment of a certain living being. Therefore, the denaturation temperature of collagen derived from scale of a fish which lives in the water, is not so high.

The fish-derived collagen contained in the fish-derived collagen membrane of the present invention is not limited by the denaturation temperature thereof. However, it is preferable that a fish-derived collagen has a high denaturation temperature. In particular, the denaturation temperature is preferably 20° C. or more, more preferably 25° C. or more, even more preferably 28° C. or more, most preferably 30° C. or more. However, the fish-derived collagen membrane can be obtained using a fish-derived collagen with a denaturation temperature at less than 20° C., by manufacturing at a temperature equal to or lower than the denaturation temperature of the fish-derived collagen.

A method for obtaining the fish-derived collagen is not particularly limited, so long as a method wherein the "triple-helix structure" of collagen may not be destroyed. For example, the fish-derived collagen can be extracted by a method disclosed in Japanese Unexamined Patent Publication (Kokai) No. 2006-257014. A method for preparing collagen from fish scales is explained below.

Firstly, the collected scales are washed in order to remove undesired substances such as fishskin and fins. If necessary, substances responsible for odor such as proteins, other than collagen, or lipids which adhere to the scale surface may be removed from scales by using alcohol such as methanol, ethanol, or isopropanol, hydrophilic organic solvent such as acetone, surfactant, salt solution such as sodium chloride solution, and alkaline solution such as sodium hydrate solution.

Next, the mineral component (calcium phosphate) included in the scales is dissolved by gently stirring with an agitating blade in a demineralizing solution for 1 to 48 hours. The demineralizing solution is not limited, so long as the mineral component can be dissolved therein. An aqueous solution of inorganic acid such as hydrochloric acid, or phosphoric acid, organic acid such as acetic acid or citric acid, ethylene diamine tetra-acetic acid, or the like, may be used. Hydrochloric acid solution or acetic acid solution, which is widely used, is preferable. The amount of demineralizing solution is not particularly limited, so long as the scales are washed with purified water after demineralization.

The scales wherein impurities are taken away, are gently stirred with an agitating blade in acidic solution containing protease for 2 to 72 hours, and whereby soluble collagen is extracted by cutting the cross-linking between collagen molecules. Subsequent steps after the above extraction step may be carried out at a temperature equal to or lower than the denaturation temperature, preferably at a temperature equal to or lower than a temperature of minus 5 degree celsius with respect to the denaturation temperature, so that the collagen is not denatured.

Pepsin, proctase, papain, protease M, or the like, which exhibits high activity in acidic solution, is preferably used as a protease. A range of pH of the solution is not limited, so long as the activity of protease is maintained high, but generally 2 to 5. The amount of protease is not particularly limited. However, 1 to 15% by weight of protease with respect to a dry weight of the fish scales is employed conventionally. A concentration of the protease and a volume of solution may be appropriately determined for the even stirring of the scales. The used acid is not particularly limited. However, hydrochloric acid, acetic acid, citric acid, malic acid or the like, which has high safety for humans, may be preferably selected, and particularly hydrochloric acid, or acetic acid is preferable. According to the method above, an atelocollagen, wherein nonhelical regions (telopeptides) presented on both sides of the collagen molecule are degraded, can be extracted.

The resulting soluble collagen is separated from insoluble fish scale residues via centrifugation or filtration. Soluble collagen can be extracted from the separated fish scale residues by treating the residues in acidic solution containing protease. Thus, high yield of soluble collagen may be obtained by repeating the extraction step approximately 2 to 4 times.

The resulting collagen solution contains protease, proteins other than collagen, gelatin (denatured collagen), and the like. Thus, if necessary, collagen can be purified from the collagen solution. A purification method of collagen is described below. Salt such as sodium chloride is added to the soluble collagen solution. As the concentration of salt is raised, collagen is precipitated. For example, collagen can be precipitated (salt out) by adding sodium chloride to a soluble collagen solution at a final concentration of 1 M and allowing it to stand for 5 minutes to 24 hours.

Collagen can be precipitated by adding sodium hydrate to the collagen solution so that the pH of the solution is raised to equal to or more than neutral pH. For example, collagen can be precipitated (salt out) by adding sodium hydrate to a soluble collagen solution at a final pH of 7 to 9 and allowing it to stand for 5 minutes to 24 hours. As the soluble collagen solution yields a white turbidity through the above procedure, precipitation of collagen may easily be confirmed.

The precipitated collagen is collected by a conventional method for separating liquids from solids, such as centrifugation or filtration, and resolved in an acidic solution by gently stirring. For example, the precipitated collagen may be gently stirred in an acidic solution of pH 2 to 4, for 1 to 48 hours. As mentioned above, collagen can be purified, and highly purified collagen can be obtained by repeating this process. Salts used in the purification step can be removed with distilled water using a dialysis membrane, etc.

(Tensile Strength)

The tensile strength of the collagen fiber membrane of the present invention is 30 MPa or more, preferably 40 MPa or more, more preferably 50 MPa or more, most preferably 55 MPa or more. When the tensile strength is less than 30 MPa, a sufficient strength when used as a biomaterial, can not be expected.

Further, the upper limit of the tensile strength is not particularly limited, but it is preferably 200 MPa or less, more preferably 150 MPa or less, most preferably 120 MPa or less. When the tensile strength is more than 200 MPa, the implanted collagen fiber membrane sometimes may not bind tissues therearound, or may cause damage to the tissues therearound.

The tensile strength test can be carried out in accordance with a conventional method. That is, both sides of a specimen having a width of 1 to 10 mm and a length of 20 to 30 mm are fixed on a tensile testing machine so that a distance between load cells is 10 mm. The specimen is pulled at a rate of 0.5 mm/minute, and stretch (%) at fracture and stress (g) at fracture are measured using the tensile testing machine (Orientec; STA-1150). The average values of five specimens are measured. Further, a specimen thickness is measured by a micrometer, and the tensile strength of the specimen is calculated.

For example, a shape of the specimen may be a rectangular shape, or a shape in which the width is 10 mm, a length of 20 mm and the center width becomes narrower from 10 mm to 5 mm. The tensile strength can be calculated from the thickness and width of the specimen.

(Young's Modulus)

Young's modulus means stress per unit strain in a range wherein the specimen has elasticity. Thus, for example, the unit of Young's modulus can be expressed as GPa which is same as the unit of stress.

Young's modulus of the collagen fiber membrane of the present invention is not particularly limited, but the lower limit is preferably 0.1 GPa or more, more preferably 0.5 GPa or more, while the upper limit is preferably 5.0 GPa or less, more preferably 2.0 GPa or less. When Young's modulus is less than 0.1 GPa, the membrane cannot be maintained in shape by itself. When Young's modulus is more than 5.0 GPa, a reduction of biocompatibility for the membrane may be expected due to an excessive hardness thereof.

(Density)

The collagen fiber membrane of the present invention has a density of 0.4 $g/cm^3$ or more, preferably 0.5 $g/cm^3$ or more, more preferably 0.6 $g/cm^3$ or more, even more preferably 0.65 $g/cm^3$ or more, most preferably 0.70 $g/cm^3$ or more, determined by the gravimetric method. When the density is less than 0.4 $g/cm^3$, mechanical strength of the collagen fiber membrane is deficient. The upper limit of the density is not particularly limited, but it is preferably 1.2 $g/cm^3$ or less, more preferably 1.15 $g/cm^3$ or less, most preferably 1.1 $g/cm^3$ or less. When the density is more than 1.2 $g/cm^3$, impurities may be contaminated to the collagen fiber membrane in the drying step. The density determined by the gravimetric method can be calculated by dividing weight by the volume of the collagen fiber membrane.

(Average Membrane Thickness)

An average membrane thickness of the collagen fiber membrane of the present invention is 1 μm to 2 mm, preferably 5 μm to 1 mm, more preferably 10 to 500 μm. When the average membrane thickness is less than 1 μm, the strength of the membrane may be significantly reduced, or a membrane with uniform thickness may not be obtained. When the average membrane thickness is more than 2 mm, it may take a long time to dry, or it may be difficult to form a membrane with uniform thickness.

The average membrane thickness can be measured in accordance with the following method. Membrane thickness of a prepared collagen fiber membrane is measured using a micrometer. Then, the average membrane thickness can be obtained by measuring at least five membrane thicknesses, thus producing an average membrane thickness.

(Variation in Membrane Thickness)

The variation in membrane thickness of the present invention is plus or minus 30% relative to the average membrane thickness. When the variation in membrane thickness is more than 30%, a part with high strength and a part with low strength are present in the collagen fiber membrane, and thus the mechanical strength, such as tensile strength, may sometimes reduce.

The variation in membrane thickness can be measured in accordance with the following method. At least five membrane thicknesses of a prepared collagen fiber membrane are measured using a micrometer. Then, the variation in membrane thickness can be obtained by calculating the standard deviation of the measured membrane thicknesses.

(Complex Fiber)

Figure 4:
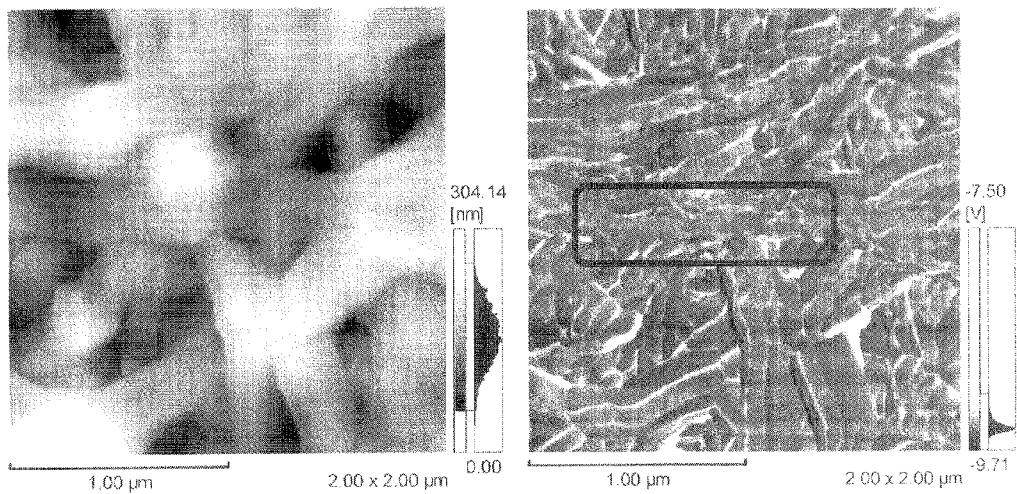
FIG. 4(A) is atomic force micrographs of the fish-derived collagen fiber membrane. The region surrounded by a black border shows a stripe periodicity structure. The striped periodicity structure is also observed in a natural fish scale's collagen fiber.
FIG. 4(B) is atomic force micrographs of the fish-derived collagen fiber membrane. The region surrounded by a black border shows a structure of collagen forming a spiral complex of collagen fibers.
Figure 4:
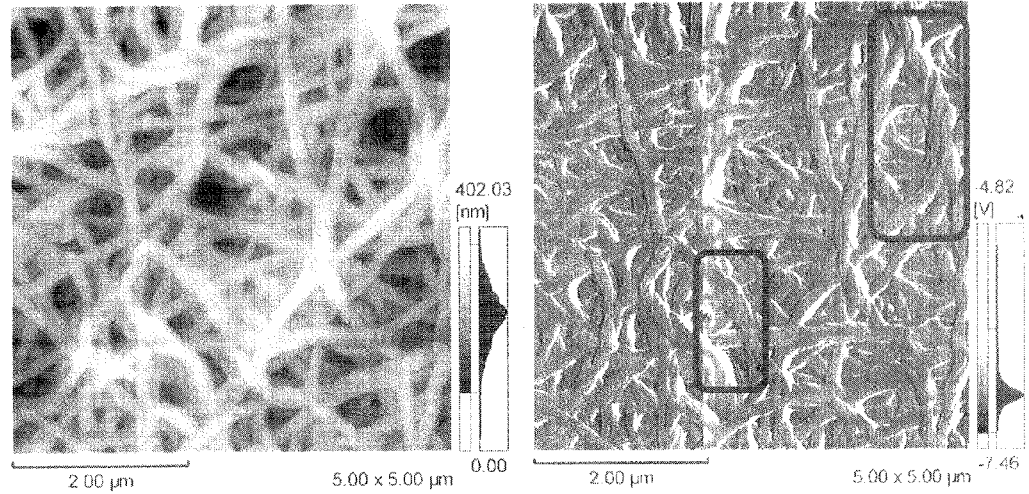

The collagen fiber membrane of the present invention, as shown in FIG. 4, preferably contains complex fiber. The collagen complex fiber means that the collagen microfibrils with a diameter of 80 to 150 nm formed from fish scale-derived collagen furthermore are partially assembled like a spindle winding fiber. A function of the spindle winding collagen complex fiber has not been clearly elucidated. However, the spindle winding collagen complex fiber is observed in collagens with high interaction of collagen fibers. Thus, it is considered that the spindle winding collagen complex fiber contributes to the increase of mechanical characteristics of the collagen fiber membrane. However, the present invention may be comprised of a collagen fiber membrane which does not contain the spindle winding collagen complex fiber. Further, even if the spindle winding collagen complex fiber does not have an effect on the mechanical characteristics of the collagen fiber membrane, the present invention is by no means limited to the explanation above.

(Cross-Linking)

The collagen fiber membrane of the present invention may be cross-linked, since the cross-linking can further increase the mechanical characteristics. Cross-linking points in a collagen fiber membrane may be occurred of the collagen molecules in the triple-helix structure, and further, of the collagen fibrils formed from the collagen molecules. There is no particular limitation to the cross-linking method. The collagen fiber membrane may be cross-linked by, for example, physical cross-linking using gamma radiation, ultraviolet radiation, heat treatment (thermal dehydration), electron beam, or the like; or chemical cross-linking using a crosslinking agent or a condensation agent. However, cross-linking using heat treatment or a crosslinking agent is preferable, because large equipments are not essential.

For example, the heat treatment may be carried out using a vacuum furnace under reduced pressure. A carboxyl group and an amino group of collagen fibers are condensed by dehydrating collagen, and the collagen fibers are effectively cross-linked.

Further, by using a crosslinking agent, the collagen fibers can be effectively cross-linked as well as the heat treatment under reduced pressure. There is no particular limitation to the crosslinking agent so long as it can form a bridge of proteins and has water solubility and volatilization ability. The crosslinking agent may form a bridge between carboxyl groups and amino groups, or simply between amino groups. As the crosslinking agent, for example, aldehyde-based crosslinking agents, carbodiimide-based crosslinking agents, epoxide-based crosslinking agents, or imidazole-based crosslinking agents is preferable in view of economic efficiency, safety, and handling. In particular, there may also be mentioned glutaraldehyde, or a water-soluble carbodiimide such as 1-(3-Dimethylaminopropyl)-3-ethylcarbodiimide hydrochloride, 1-cyclohexyl-3-(2-morpholinyl-4-ethyl) carbodiimide sulfonate or the like.

(Degree of Cross-Linking)

The level of cross-linking of the collagen fiber membrane can be defined by a degree of cross-linking. A method for defining the degree of cross-linking is not limited. For example, when the collagen fiber membrane is cross-linked by glutaraldehyde, amino groups of the collagen are expended. Thus, the degree of cross-linking can be measured by quantifying free amino groups of the collagen fiber membrane. Specifically, an amount of free amino groups are measured by a TNBS method using trinitrobenzene sulfonate.

There is no particular limitation to the degree of cross-linking of the collagen fiber membrane of the present invention. However, a lower limit of the degree of cross-linking is preferably 5% or more, more preferably 15% or more, most preferably 30% or more. An upper limit of the degree of cross-linking is preferably 90% or less, more preferably 80% or less, most preferably 75% or less. When the degree of cross-linking is less than 5%, the collagen fiber membrane is easily degraded by proteases. When the degree of cross-linking is more than 90%, the collagen fiber membrane is hardly degradable in vivo.

(Denaturation Temperature)

Collagen, in general, is changed to gelatin in increasing temperature and at that time the triple-helix structure is destroyed, of which temperature be called denaturation temperature.

The denaturation temperature of the collagen fiber membrane of the present invention is increased significantly due to the structure thereof, compared to a denaturation temperature of the collagen before fibril formation. That is to say, the collagen fiber membrane of the present invention is thermally-resistant.

There is no limitation to the denaturation temperature of the collagen fiber membrane of the present invention. However, the denaturation temperature of the collagen fiber membrane is higher than that of collagen before fibril formation by preferably 3° C. or more, more preferably 5° C. or more, even more preferably 8° C. or more. Furthermore, the denaturation temperature of the cross-linked collagen fiber membrane is higher than a denaturation temperature of collagen before fibril formation by preferably 10° C. or more, more preferably 15° C. or more, even more preferably 20° C. or more, most preferably 25° C. or more. Due to the high denaturation temperature, the collagen fiber membrane is thermally-resistant, and thus, the collagen fiber membrane of the present invention can be used in various applications. The upper limit of the denaturation temperature is not particularly limited, but preferably 200° C. or less, more preferably 90° C. or less.

(Swelling Ratio)

The collagen fiber membrane of the present invention has a low swelling ratio, and thus the collagen fiber membrane is water-resistant.

There is no particular limitation to the swelling ratio of the collagen fiber membrane of the present invention. However, the upper limit of the swelling ratio is preferably 300% or less, more preferably 250% or less. The lower limit of the swelling ratio is 100% or more. The term "swelling ratio of 100%", as used herein, means that the collagen fiber membrane does not swell at all. When the swelling ratio is more than 300%, the strength of the collagen fiber membrane is reduced by rapid swelling, and then the collagen fiber membrane is degraded rapidly in vivo.

<<Induction of Osteoblast Differentiation>>

The collagen fiber membrane of the present invention can induce a differentiation of mesenchymal stem cells into osteoblasts. In particular, mesenchymal stem cells may differentiate into osteoblasts by bringing into contact the collagen fiber membrane with mesenchymal stem cells or culturing mesenchymal stem cells using the collagen fiber membrane. Particularly, the collagen fiber membrane exhibits an excellent inducibility of differentiation in early stages. The collagen fiber membrane for a cell culture substrate has a certain, preferable level of strength. The high-strength collagen fiber membrane is useful as the collagen fiber membrane for induction of osteoblast differentiation, in view of the strength thereof.

(Mesenchymal Stem Cells)

Mesenchymal stem cells are not limited, so long as they can differentiate into osteoblasts, but they include bone marrow mesenchymal stem cells, adipose tissue-derived mesenchymal stem cells, synovial tissue-derived mesenchymal stem cells, dental pulp-derived mesenchymal stem cells, dental germ-derived mesenchymal stem cells, auricular cartilage-derived mesenchymal stem cells, peripheral blood mesenchymal stem cells, umbilical cord blood-derived mesenchymal stem cells, ligament-derived mesenchymal stem cells, tendon-derived mesenchymal stem cells, ES cell-derived mesenchymal stem cells, or iPS cell-derived mesenchymal stem cells. Further, there are no particular limitations to animate beings from which the mesenchymal stem cells are derived. As for mammals, there may be mentioned, for example, human, primate simian, canine, feline, swine, sheep, goat, bovine, horse, rabbit, guinea pig, rat, and mouse. As for birds, there may be mentioned chicken, quail, duck, goose, ostrich, and guinea fowl. As for reptiles, there may be mentioned gator, turtle, and skink. As for amphibians, there may be mentioned flag, and newt. As for fish, there may be mentioned tilapia, sea bream, bastard halibut, shark, and salmon. Further, as for invertebrates, there may be mentioned crab, shellfish, jellyfish, and shrimp.

The mesenchymal stem cells have a potency of differentiation into mesenchymal cells such as osteoblasts, adipose cells, muscle cells, or cartilage cells, and may differentiate into cells which compose bone, blood vessel, or cardiac muscle.

As for the mesenchymal stem cells, an established cell line may be used. Further, in accordance with the conventional method, the mesenchymal stem cells can be arranged. Furthermore, as for the mesenchymal stem cells, commercially-available mesenchymal stem cells may be used. Furthermore, the mesenchymal stem cells (such as bone marrow mesenchymal stem cells, adipose tissue-derived mesenchymal stem cells, synovial tissue-derived mesenchymal stem cells, dental pulp-derived mesenchymal stem cells, dental germ-derived mesenchymal stem cells, auricular cartilage-derived mesenchymal stem cells, peripheral blood mesenchymal stem cells, umbilical cord blood-derived mesenchymal stem cells, ligament-derived mesenchymal stem cells, tendon-derived mesenchymal stem cells, ES cell-derived mesenchymal stem cells, or iPS cell-derived mesenchymal stem cells) separated from a living body can differentiate into osteoblasts via a method of osteoblast differentiation induction in the present invention. In this case, preferably, cells are separated from connective tissues etc. in accordance with the conventional method, and then prepared. Further, as for the mesenchymal stem cells collected and prepared from a living body, it is preferred that primary cultured cells are used. Subcultured cells may be used, but the fewer number of subculturing, the better. For example, the number of subculturing is preferably 10 or less, more preferably 5 or less, most preferably 2 or less.

(Osteoblast)

The osteoblasts form bone in bone tissue, of which cytoplasm is basophilic, and has alkaline phosphatase activity. Further, the osteoblasts may have androgen receptors and/or estrogen receptors. Androgen decreases osteoblast activity, and estrogen stimulates osteoblasts. The induction of osteoblast differentiation from mesenchymal stem cells into osteoblasts may be confirmed through measurement of the alkaline phosphatase activity. The measurement of alkaline phosphatase activity may be carried out by conventional methods as shown in the Examples.

(Contact and Culture)

A culture medium used in contact between the collagen fiber membrane and mesenchymal stem cells, or culture of mesenchymal stem cells using the collagen fiber membrane, is not limited, as long as the mesenchymal stem cells can be maintained therein. Generally, the culture medium for culturing the mesenchymal stem cells may be used. For example, a conventional medium such as an MEM medium, α-MEM medium, or D-MEM medium can be appropriately selected in accordance with the cultured cells.

The contact time or culture time is not limited, so long as the mesenchymal stem cells differentiate into osteoblasts. Substantially, the lower limit of contact time or culture time is 10 minutes or more, preferably 1 hour or more, more preferably 1 day or more. The lower limit of contact time or culture time is also not limited, preferably 30 days or less, more preferably 15 days or less, even more 7 days or less.

The contact temperature or culture temperature may be appropriately determined in accordance with most suitable culture temperatures of used mesenchymal stem cells. For example, in mammal mesenchymal stem cells, the contact temperature or culture temperature is 30° C. to 40° C., preferably 35° C. to 37° C. However, the mesenchymal stem cells may be brought into contact with the collagen fiber membrane at a temperature higher or lower than the culture temperature. For example, when the fish-derived collagen with a low denaturation temperature is used, the mesenchymal stem cells are brought into contact with the cell culture substance at a temperature lower than the culture temperature, and then the mesenchymal stem cells can be cultured at the most suitable culture temperature.

(Osteoblast Differentiation Factor)

In the contact between the collagen fiber membrane and mesenchymal stem cells, or the culture of mesenchymal stem cells using the collagen fiber membrane, an osteoblast differentiation factor may be added thereto. There is no limit to the osteoblast differentiation factor, as long as the mesenchymal stem cells can differentiate into osteoblasts by the osteoblast differentiation factor. For example, an immune suppressor such as dexamethasone, FK-506, or cyclosporine, bone morphogenic protein (BMP) such as BMP2, BMP4, BMP5, BMP6, BMP7, or BMP9, bone morphogenetic humoral factor such as TGFβ may be mentioned. One or more osteoblast differentiation factors selected from the above osteoblast differentiation factors can be added to the culture medium.

A concentration of the osteoblast differentiation factor may be appropriately determined in accordance with the type of osteoblast differentiation factor. For example, dexamethasone can be used at a concentration of 1 to 100 nM. In particular, it can be used, preferably, at a concentration of 10 nM.

(Function)

In the collagen fiber membrane whereby the mesenchymal stem cells can differentiate into osteoblasts, it is important that the collagen fiber membrane is prepared using the fish-derived collagen, preferably the fish scale-derived collagen. That is to say, swine-derived or bovine-derived collagen cannot cause a differentiation of mesenchymal stem cells into osteoblasts.

Further, as shown in the Examples, the inducibility of differentiation of the collagen transparent membrane wherein the collagen fibril does not form, is low. These results indicated that the collagen fibril formation is important for the differentiation of mesenchymal stem cells into osteoblasts.

The mechanism, wherein the mesenchymal stem cells can differentiate into osteoblasts by using the high-strength collagen fiber membrane of the present invention, has not been fully elucidated, but is presumed to be as follows. It is considered that the differentiation of the mesenchymal stem cells into osteoblasts (particularly differentiation in the early stages) may be induced by bringing the collagen fiber membrane and the mesenchymal stem cells into contact with one another.

[2] Method for Preparing a Fish-Derived Collagen Fiber Membrane

The method for preparing a fish-derived collagen fiber membrane comprises the steps of: (1) forming a collagen fibril from a soluble collagen in a collagen solution, to obtain a collagen fiber gel of 0.3% by weight or more (hereinafter referred to as a collagen fibril formation step), (2) removing a salt from the collagen fiber gel using purified water and ethanol (hereinafter referred to as a salt removal step), and (3) drying the collagen fiber gel by covering a lower surface and an upper surface of the collagen fiber gel and removing a solvent from a side of the collagen fiber gel (hereinafter referred to as a solvent removal and drying step).

The "fish-derived collagen fiber membrane of the present invention" may be prepared by the preparation method of the same of the present invention. However, the fish-derived collagen fiber membrane of the present invention can be prepared by a preparation method other than the preparation method of the present invention.

(Fish-Derived Collagen)

As a fish-derived collagen used in the method for preparing the fish-derived collagen fiber membrane of the present invention, the fish-derived collagen described in the above item "[1] Fish-derived collagen fiber membrane" can be used.

(Collagen Fibril Formation Step)

In the collagen fibril formation step, the collagen fibrils are formed from soluble collagen in a collagen solution. For example, the soluble collagen solution may be obtained by dissolving the fish-derived collagen in an acidic aqueous solvent. That is, the soluble collagen solution can be prepared by mixing an inorganic acid or organic acid with an aqueous solvent, and dissolving the collagen in the mixture. The inorganic acid includes hydrochloric acid, phosphoric acid, nitric acid, and sulfuric acid. The organic acid includes acetic acid, formic acid, citric acid, and oxalic acid. The pH of the soluble collagen solution is preferably pH 2.0 to 4.0.

Further, the soluble collagen solution may be prepared using a carbon dioxide solution with a pH of 4 or less, wherein carbon dioxide is solved by bubbling $CO_2$. That is, the soluble collagen solution can be prepared by dissolving the fish-derived collagen in the acidic carbon dioxide solution.

The soluble collagen solution is adjusted to an appropriate ionic strength and pH, whereby the fish-derived collagen forms collagen fibrils. That is to say, the fish-derived collagen fibrils are formed through the addition of an appropriate buffer solution to the soluble collagen solution. The optimal pH level for fibril formation of the fish-derived collagen varies in accordance with the type of fish-derived collagen. However, many types of fish-derived collagen may form the collagen fibrils at a range of pH 5 to pH 9, i.e. neutral pH, and therefore neutral buffers are frequently used for fibril formation. There is no particular limitation to the buffer, as long as it may has appropriate ionic strength and neutral pH condition. However, in view of a practical application, such as an artificial bone implanted in a living body, an aqueous solution containing salt, which has a buffering ability, such as a phosphate buffer, an acetate buffer, a carbonate buffer, a citrate buffer, or a Tris buffer, which has low cytotoxicity or lack cytotoxicity, is preferable. In particular, a phosphate buffer (such as Dulbecco's PBS, or sodium phosphate buffer) is preferable because it is an inexpensive, neutral buffer that does not exhibit toxicity to a living body, and has an excellent collagen fibril formation ability compared with other neutral buffers.

A collagen fiber gel obtained in the collagen fibril formation step has a collagen concentration of 0.3% by weight or more, preferably 0.4% by weight or more, most preferably 0.5% by weight or more. When the collagen concentration is less than 0.3% by weight, it is difficult to prepare collagen fiber gel with sufficient strength.

(Salt Removal Step)

In the salt removal step, salt is removed from the collagen fiber gel using the purified water and lower alcohol mixtures. In particular, a solvent containing salt in the collagen fiber gel is replaced by a graded series of purified water and lower alcohol. The lower alcohol having 1 to 4 carbon atoms i.e. methanol, ethanol, n-propyl alcohol, isopropyl alcohol, n-butyl alcohol, isobutyl alcohol, sec-butyl alcohol, or tert-butyl alcohol, can be used. Further, water and lower alcohol gradual mixture ratios may be appropriately determined. For example, as the graded series of water and lower alcohol, an ethanol solution of 50% by volume, an ethanol solution of 70% by volume, an ethanol solution of 90% by volume, and 100% ethanol can be used to replace the solvent contained in the collagen fiber gel by 100% ethanol.

By replacing the solvent with the lower alcohol, the collagen fiber gel can be rapidly dried in the following solvent evaporation and drying step.

(Solvent Removal and Drying Step)

In the solvent evaporation and drying step, the purified water and/or lower alcohol are removed and the collagen fiber gel is dried. By the solvent evaporation and drying step, there is an increase in the density of the fish-derived collagen, and the strength thereof also increase.

The solvent evaporation and drying are carried out as follows. A lower surface and an upper surface of the gel are covered by a flat and smooth plate capable of preventing a transmission of water and alcohol etc., and the solvent is gently evaporated only from a side of the collagen fiber gel. By covering the gel with the flat and smooth plate, the fish-derived collagen fiber membrane having an even thickness may be obtained, and thus the mechanical strength of the collagen fiber membrane can be increased. There is no limitation to the material of the plate, but there may be mentioned polystyrene, silicone, polyester, polyamide, polypropylene, polyethylene, polymethylmethacrylate or glass. Specifically, polystyrene is preferable because it exhibits an excellent, dissociating property from the fish-derived collagen fiber membrane.

Time for evaporating solvent and drying is not particularly limited, so long as the purified water and alcohol of 90% or more may be removed, but preferably 1 hour to 13 days, more preferably 3 hours to 7 days, most preferably 5 hours to 24 hours.

(Cross-Linking Step)

Further, a cross-linking step of the fish-derived collagen fiber membrane may be included in the method for preparing a fish-derived collagen fiber membrane of the present invention. In the collagen fiber membrane, the collagen molecules (tropocollagen) in the collagen fiber membrane may be cross-linked with one another, and the collagen fibrils formed by the collagen molecules (tropocollagen) may be cross-linked with one another.

In regards to cross-linking procedure, the conventional procedure may be used. For example, the physical cross-linking or chemical cross-linking may be used. The physical cross-linking includes thermal cross-linking (cross-linking by thermal dehydration; DHT), cross-linking using ultraviolet (UV) radiation, or cross-linking using gamma radiation. In the thermal cross-linking, the collagen fiber membrane is allowed to stand at 100° C. to 140° C. for 1 to 12 hours in a vacuum. However, the collagen may be denatured by the high-temperature treatment. Therefore, chemical cross-linking which is carried out at a temperature equal to or lower than the denaturation temperature, is preferable.

As the crosslinking agent used in chemical cross-linking, a chemical crosslinking agent such as glutaraldehyde, polyepoxy compound, carbodiimide, isocyanate, or genipin, can be used. In chemical cross-linking, the collagen fiber membrane is cross-linked by immersing the collagen fiber membrane in a solvent containing the crosslinking agent. In the case of glutaraldehyde, for example, the collagen fiber membrane can be uniformly cross-linked in a glutaraldehyde solution of 0.5% to 2.0% by weight. Preferably, however, the collagen fiber membrane is treated at approximately 20° C. to 40° C. for 1 hour to 24 hours under reduced pressure, in a desiccator including a 25% glutaraldehyde solution or a diluted solution thereof. An inner part of the collagen fiber membrane can also be uniformly cross-linked through glutaraldehyde evaporation. The collagen fiber membrane strength is increased through cross-linking.

EXAMPLES

The present invention will now be further illustrated by, but is by no means limited to, the following Examples.

Preparing Example 1

Preparation of Fish-Derived Collagen

A method for preparing tilapia scale collagen will be described hereinafter.

The tilapia scales were carefully washed with water, and further carefully washed in a 10% sodium chloride solution. Impurities such as fins were removed during washing, and then the tilapia scales were dried at room temperature. A water content ratio of the tilapia scales was 18.5% by weight. 1 kg of tilapia scales were dispersed in 9 kg of hydrochloric acid solution at pH 2, and the solution including the scales was gently stirred at 25° C., while maintaining pH 2, by adding a 1 M hydrochloric acid solution. Through the above treatment, mineral elements included in the scales were dissolved in the hydrochloric acid solution. The scales were collected by mesh, and then fully washed with purified water. Then, the hydrochloric acid solution at pH 2 was added to the scales so that the total weight of the whole was 4 kg.

Then, 24 g of pepsin (Wako Pure Chemical Industries, Co., Ltd.; 1:10000) was added to the whole, and the whole was gently stirred at 25° C., for 24 hours using an agitating blade, whereby collagen was dissolved into the hydrochloric acid solution from the scales. A soluble collagen solution was separated from scale residues by mesh, and then the supernatant was collected by centrifugation (10000 G, for 60 minutes) so that the soluble collagen solution was separated from the fine scale residues. 0.5 g of pepsin was added to the soluble collagen solution and the mixture was allowed to stand at 25° C., for 24 hours.

The resulting solution (2.4 kg) was filtered with 0.45 μm of a membrane filter. Then, sodium chloride was added to give 1.0 M of the final concentration, and the whole was gently stirred. After salting-out at 25° C., for 30 min, the supernatant was removed by centrifugation (10000 G, for 20 minutes), and the precipitate of collagen was collected. 400 mL of hydrochloric acid solution at pH 2 was added to the precipitate, and the collagen was dissolved in the solution by gently stirring at 5° C., for 24 hours. The above purification step of salting-out was repeated three times, and the hydrochloric acid solution containing the tilapia scale collagen was obtained.

Examples 1 to 3 and Comparative Examples 1 to 3

In this example, the high-strength collagen fiber membrane was prepared using the collagen fiber gel with a 5 mm thickness.

Figure 1:
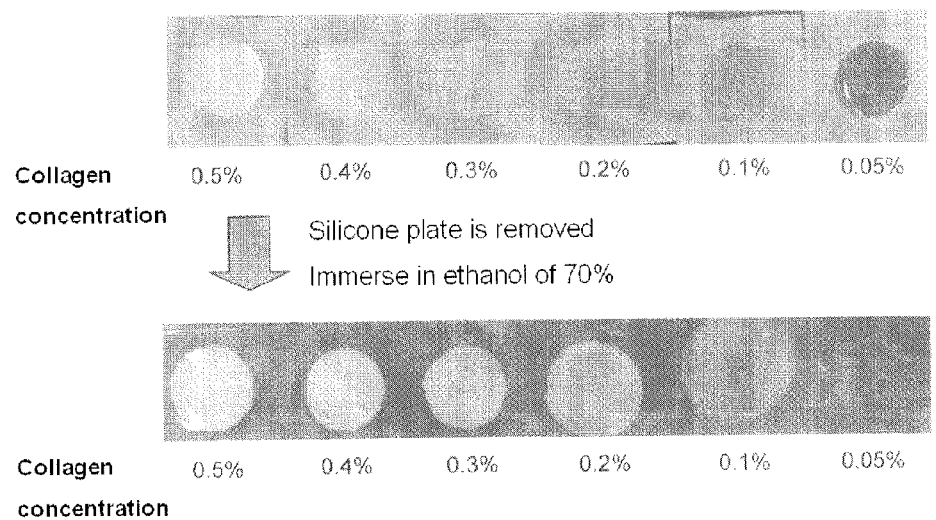
FIG. 1 is a photograph showing the collagen fiber gels prepared using hydrophilic acid solution containing 0.5% by weight (Example 1), 0.4% by weight (Example 2), 0.3% by weight (Example 3), 0.2% by weight (Comparative Example 1), 0.1% by weight (Comparative Example 2), or 0.05% by weight (Comparative Example 3) of tilapia scale-derived collagen.

The hydrochloric acid solution containing tilapia scale collagen obtained in Preparing Example 1 was diluted to a concentration of 0.5% by weight (EXAMPLE 1), 0.4% by weight (EXAMPLE 2), 0.3% by weight (EXAMPLE 3), 0.2% by weight (COMPARATIVE EXAMPLE 1), 0.1% by weight (COMPARATIVE EXAMPLE 2), or 0.05% by weight (COMPARATIVE EXAMPLE 3) of tilapia scale collagen with the hydrochloric acid solution (0.001 mol/L, pH3.0). For example, 9 parts by volume of the hydrochloric acid solution containing 0.5% by weight of tilapia scale collagen and 1 part by volume of 10× Dulbecco's PBS (calcium and magnesium free) were mixed. The resulting mixture was poured into a mold made of silicone (silicone container) having a diameter of 18 mm and a height of 5 mm. An upper surface and a lower surface of the silicone mold were covered by slide glasses so as to prevent water evaporation, and the collagen fibril was formed at 28° C., for 3 hours. The resulting collagen fiber gel was immersed in the mixture of purified water and ethanol containing 70% by volume of ethanol (ethanol solution of 70% by volume). Sizes of the collagen fiber gel immersed in the mixture are shown in FIG. 1. It was confirmed that sizes of the collagen fiber with a collagen concentration of 0.3% by weight were maintained.

Figure 2:
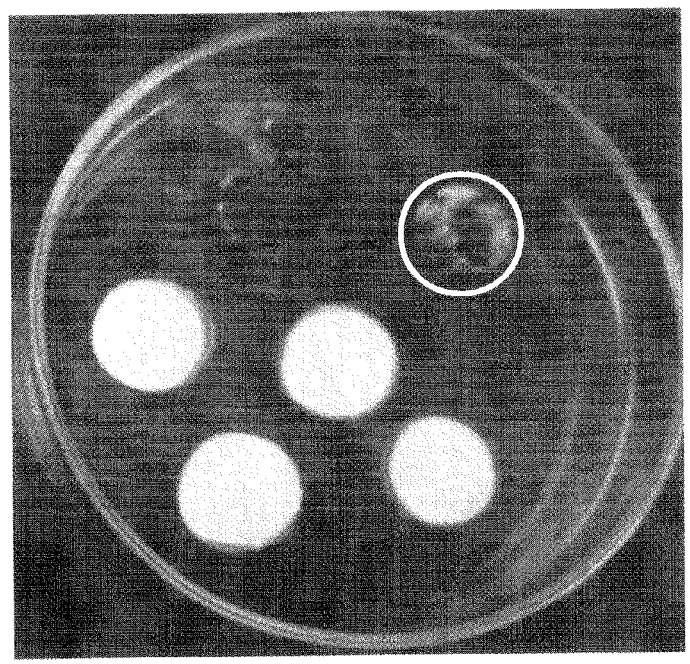
FIG. 2 is a photograph showing the fish scale-derived collagen fiber membrane after a completion of a solvent-evaporating and drying step in Example 2 (0.4% by weight of tilapia scale-derived collagen). The white circle shows remaining residues of the collagen fiber membrane, which had strongly adhered to grass when the collagen fiber membrane was separated therefrom.

The collagen fiber gel (0.4% by weight) in EXAMPLE 2 was immersed in a graded ethanol series such as an ethanol solution of 50% by volume, an ethanol solution of 70% by volume, an ethanol solution of 90% by volume, and 100% ethanol in this order, to remove salt. Then, an upper surface and a lower surface of the collagen fiber gel were covered by cover glasses or polystyrene plates, and then a solvent was removed only from a side of the collagen fiber gel for 1 day, to obtain the collagen fiber membrane. Each collagen fiber membrane can be sufficiently dried for 1 day, and the collagen fiber membranes having even thickness are obtainable. In the case of the polystyrene plates, it was easier to separate between the collagen fiber membrane and polystyrene plates. However, in the case of cover glasses, the collagen fiber membrane strongly attached on the cover glass (FIG. 2).

Example 4

In EXAMPLES 4 to 6, the high-strength collagen fiber membrane was prepared using a hydrochloric acid solution containing 1% by weight of collagen.

The procedures of Example 2 were repeated, except that the hydrochloric acid solution containing 1% by weight of tilapia scale collagen was used instead of the hydrochloric acid solution containing 0.4% by weight of tilapia scale collagen. The volume of the collagen gel was 1.271 $cm^3$ and the weight of collagen contained therein was 11.44 mg, before drying. The dried collagen fiber membrane had an even thickness of 52.5±7 μm. Further, the density of the resulting collagen fiber membrane was 0.857 $g/cm^3$.

Example 5

The procedures in Example 4 were repeated except that the silicone mold with a diameter of 18 mm and a height of 1 mm was used instead of the silicone mold with a diameter of 18 mm and a height of 5 mm. The volume of the collagen gel was 0.254 cm$^3$ and the weight of collagen contained therein was 2.28 mg, before drying. The dried collagen fiber membrane had an even thickness of 11.5±3 μm. Further, the density of the resulting collagen fiber membrane was 0.782 g/cm$^3$.

Example 6

The procedures of Example 4 were repeated, except that the silicone mold having a diameter of 18 mm and a height of 0.5 mm was used in place of the silicone mold having a diameter of 18 mm and a height of 5 mm. The volume of the collagen gel was 0.127 cm$^3$ and the weight of collagen contained therein was 1.15 mg, before drying. The dried collagen fiber membrane had an even thickness of 6.7±1 μm. Further, the density of the resulting collagen fiber membrane was 0.672 g/cm$^3$.

Comparative Example 4

The procedures of Example 4 were repeated, except that only the lower surface of the collagen fiber gel was covered by polystyrene plates, and the collagen fiber gel was dried, to obtain a collagen fiber membrane. There is no even thickness for the resulting collagen fiber membrane. That is to say, the collagen fiber membrane has thin parts, and thus, the tensile strength thereof can not be measured.

Comparative Example 5

The procedures of Example 5 were repeated, except that only the lower surface of the collagen fiber gel was covered by polystyrene plates, and the collagen fiber gel was dried, to obtain a collagen fiber membrane. The resulting collagen fiber membrane does not have an even thickness. That is to say, the collagen fiber membrane has thin parts, and thus the tensile strength thereof cannot be measured.

Comparative Example 6

The procedures of Example 6 were repeated, except that only the lower surface of the collagen fiber gel was covered by polystyrene plates, and the collagen fiber gel was dried, to obtain a collagen fiber membrane. The resulting collagen fiber membrane does not have an even thickness. That is to say, the collagen fiber membrane has thin parts, and thus the tensile strength thereof cannot be measured.

<<Structure of Collagen Membrane>>

Figure 3:
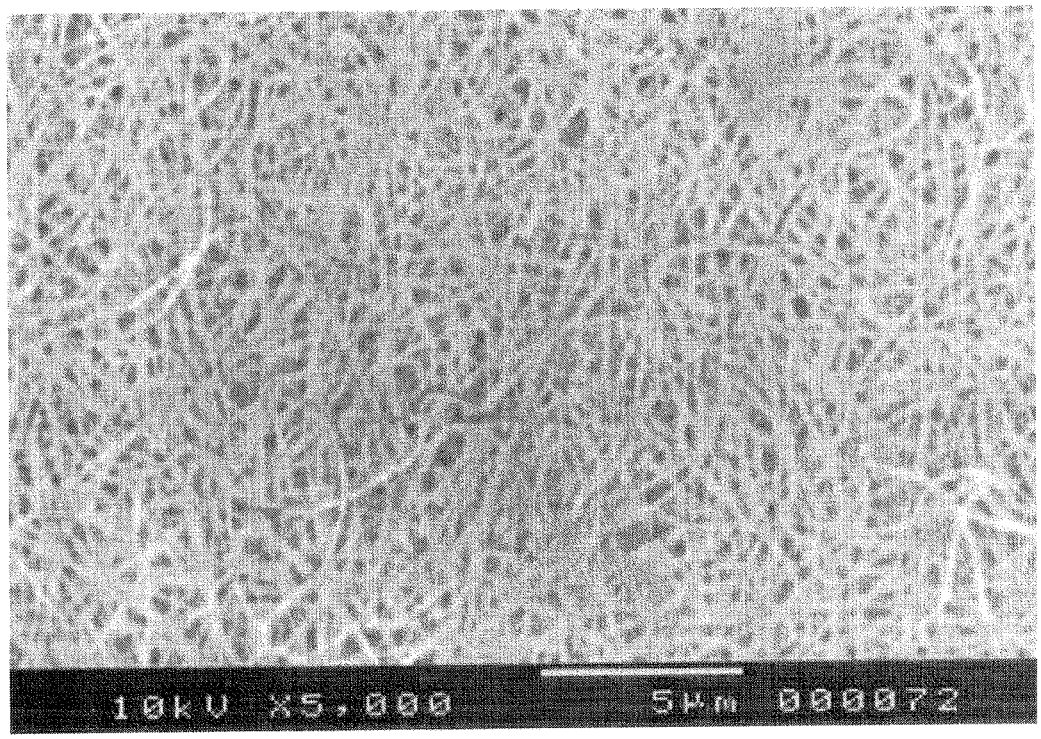
FIG. 3 is a scanning electron micrograph of the fish-derived collagen fiber membrane.

The scanning electron micrograph of the surface of the collagen fiber membrane obtained in EXAMPLE 5 is shown in FIG. 3. The collagen fiber membrane has a structure wherein the collagen fibrils are evenly tangled.

The atomic force micrographs of the structure of the collagen fiber membrane are shown in FIG. 4. The striped periodicity structures (about 60 nm), which are similar to collagen fibrils in vivo, were observed (FIG. 4A). Further, it was found that spiral complexes of collagen fibrils were formed (FIG. 4B).

<<Tensile Strength Test>>

The tensile strength test was carried out.

The procedures of Example 4 were repeated, except that the polystyrene mold having a width of 45 mm, a length of 70 mm and a height of 1 mm was used in place of the silicone mold having a diameter of 18 mm and a height of 5 mm to obtain the collagen fiber membrane.

For the tensile strength test, the resulting collagen fiber membrane was cut off in order to obtain the strip specimen with a width of 10 mm and a length of 20 to 30 mm. The membrane thickness measured by a micrometer was 6.7±1.2 μm.

Both sides of the specimen were fixed on glass and a tensile strength test was carried out using the tensile tester (Orientec; STA-1150). The distance between load cells was 10 mm, and the specimen was pulled at a rate of 0.5 mm/minute. The results are shown in FIG. 5.

Figure 5:
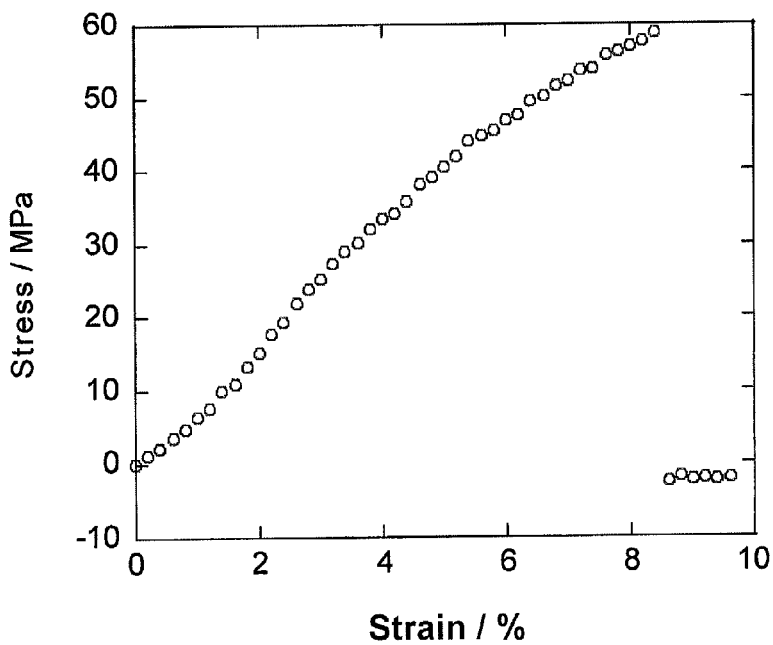
FIG. 5 is a graph showing the results of a tensile strength test of the fish-derived collagen fiber membrane.

Stress was increased gradually in proportion to strain, and the specimen was fractured at a strain of about 8.2%, as shown in FIG. 5. The maximum stress was 59 MPa.

Example 7

In this Example, the high-strength collagen fiber membrane was prepared using a hydrochloric acid solution containing 1.11% by weight of collagen.

The hydrochloric acid solution containing tilapia scale collagen obtained in Preparing Example 1 was diluted to a concentration of 1.11% by weight of tilapia scale collagen with the hydrochloric acid solution (0.0001 mol/L, pH4.0). 9 parts by volume of the hydrochloric acid solution containing 1.11% by weight of collagen and 1 part by volume of 10× Dulbecco's PBS were mixed. The resulting mixture was poured into a silicone mold with a diameter of 20 mm and a height of 2.5 mm, under which a glass plate was placed. An upper surface of the silicone mold was covered by slide glasses so as to prevent water evaporation, and the collagen fibril was formed at 28° C., for 2 hours. The resulting collagen fiber gel was immersed in a graded ethanol series such as 50% by volume of an ethanol solution, 70% by volume of an ethanol solution, and 90% by volume of an ethanol solution in this order, to remove salt. Finally, the collagen fiber gel was immersed in 99.9% by volume of an ethanol solution.

Figure 6:
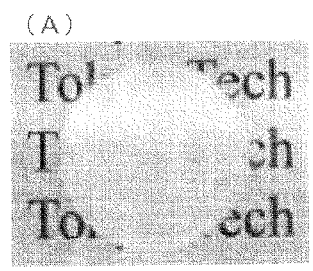
FIG. 6(A) is a photograph showing the collagen fiber membrane of Example 7, which is prepared using hydrophilic acid solution containing about 1.11% by weight of tilapia scale collagen, by covering an upper surface and a lower surface of the collagen fiber gel.
FIG. 6(B) is a photograph showing the collagen fiber membrane of Comparative Example 7, which is prepared using hydrophilic acid solution containing about 1.11% by weight, by not covering an upper surface of the collagen fiber gel.
FIG. 6(C) is a scanning electron micrograph showing the collagen fiber membrane of Comparative Example 7.
Figure 6:
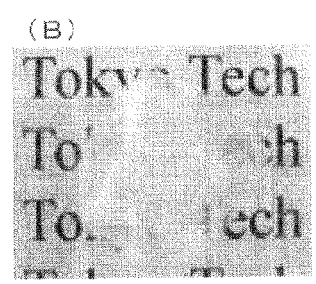
Figure 6:
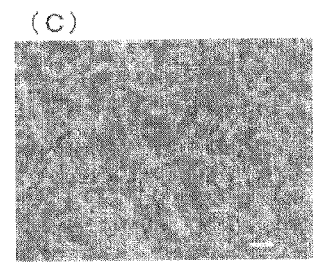

The resulting collagen fiber gel was covered by a polystyrene plate and a solvent was removed from a side thereof. The shape of the membrane after solvent removal is shown in FIG. 6A. It is found that no contraction or hole was observed on the collagen membrane that was formed, and thus the collagen membrane was uniform. Further, in accordance with the observation of structure by the electron-scanning microscope, the collagen membrane and the one shown in FIG. 3 have similar structure.

Comparative Example 7

In this Comparative Example, a collagen fiber membrane was prepared by carrying out the solvent removal and drying step without the use of a polystyrene plate.

The procedures of Example 7 were repeated, except that the solvent removal and the drying step were carried out without the use of a polystyrene plate at the upper surface. The shape of the membrane after drying is shown in FIG. 6B. The resulting collagen membrane was warped in form. Further, the collagen membrane consisting of transparent parts and opaque parts was non-uniform. As is obvious from the scanning-electron micrograph of FIG. 6C, the formation of collagen fibril can not be maintained.

Examples 8 to 13

Figure 7:
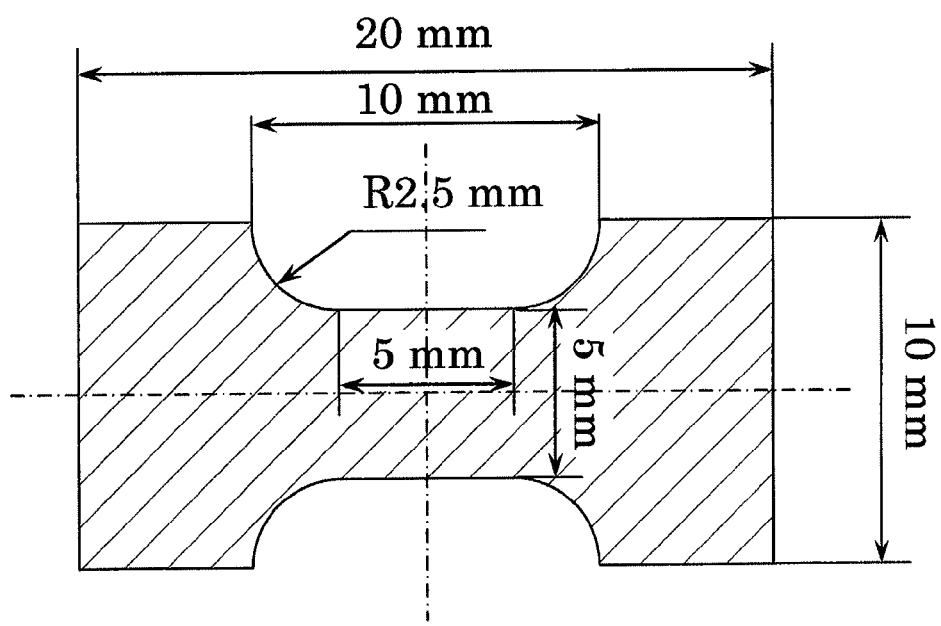
FIG. 7 is a top view of a silicone container for specimen preparation, in which the center width is 5 mm. This is for a tensile strength test.

In these Examples, the high-strength collagen fiber membranes were subjected to chemical cross-linking treatment (glutaraldehyde cross linking). Tilapia scale collagen was diluted to a concentration of 1.11% by weight of tilapia scale collagen with the hydrochloric acid solution (0.0001 mol/L, pH4.0). Nine parts by volume of the hydrochloric acid solution containing 1.11% by weight of collagen and 1 part by volume of 10× Dulbecco's PBS were mixed. The resulting mixture was poured into a silicone container under which a glass plate was placed (FIG. 7). An upper surface and a lower surface of the silicone container were covered by slide glasses so as to prevent water evaporation, and the collagen fibril was formed at 28° C., for 2 hours. The resulting collagen fiber gel was immersed in a graded ethanol series such as 50% by volume of an ethanol solution, 70% by volume of an ethanol solution, and 90% by volume of an ethanol solution in this order, to remove salt. Finally, the collagen fiber gel was immersed in 99.5% by volume of an ethanol solution. The upper surface and lower surface of the resulting collagen fiber gel were covered by polystyrene plates and solvent was evaporated from a side thereof. The polystyrene plate is smaller than the container shown in FIG. 7 by 1 mm.

20 mL of 10% glutaraldehyde solution and the resulting membrane were placed on a mesh in an incubater, and the membrane was allowed to stand at 37° C., under reduced pressure. The specimens were treated for 0 min (EXAMPLE 8), 15 min (EXAMPLE 9), 30 min (EXAMPLE 10), 1 hour (EXAMPLE 11), 2 hours (EXAMPLE 12), or 3 hours (EXAMPLE 13). Collagens in the collagen fiber membrane can be cross-linked to each other, by the vaporized glutaraldehyde. When the treatment time by glutaraldehyde was prolonged, the membrane turned brownish.

<<Measurement of the Degree of Cross-Linking>>

The degree of cross-linking of the resulting cross-linked and high-strength collagen fiber membrane was measured. The degree of cross-linking was quantified by the measurement of the amount of free amino groups by means of the TNBS method using trinitrobenzene sulfonate.

10 mg of a specimen was weighed from each collagen fiber membrane prepared in Examples 9 to 13. 1.0 mL of sodium hydrogen carbonate(4% (w/v))/TNBS(0.5% (w/v)) solution was added to the specimen, and the specimen was treated at 40° C., for 2 hours. Further, 3 mL of hydrochloric acid (6N) was added thereto, with the whole treated for 20 to 40 min, at 40° C. in a water bath. After hydrolyzing, 15 mL of purified water was added to the whole. 1 mL of solution was collected, cooled to room temperature, and diluted using 5 mL of purified water. Then, the absorbance at a wavelength of 345 nm of the resulting solution was measured. The amount of free amino groups was calculated using the following formula:

Amount of free amino group($A_{g\text{-}col}$;mol)/amount of collagen (g)=(4×absorbance)/(1.46×10⁶ (L/mol·cm)·length of cell (cm))

The amount of free amino group ($A_{col}$) was measured by TNBS method using untreated collagen. The degree of cross-linking (D;%) was calculated using the following formula:

$(1-A_{g\text{-}col}/A_{col})\times 100$

Figure 8:
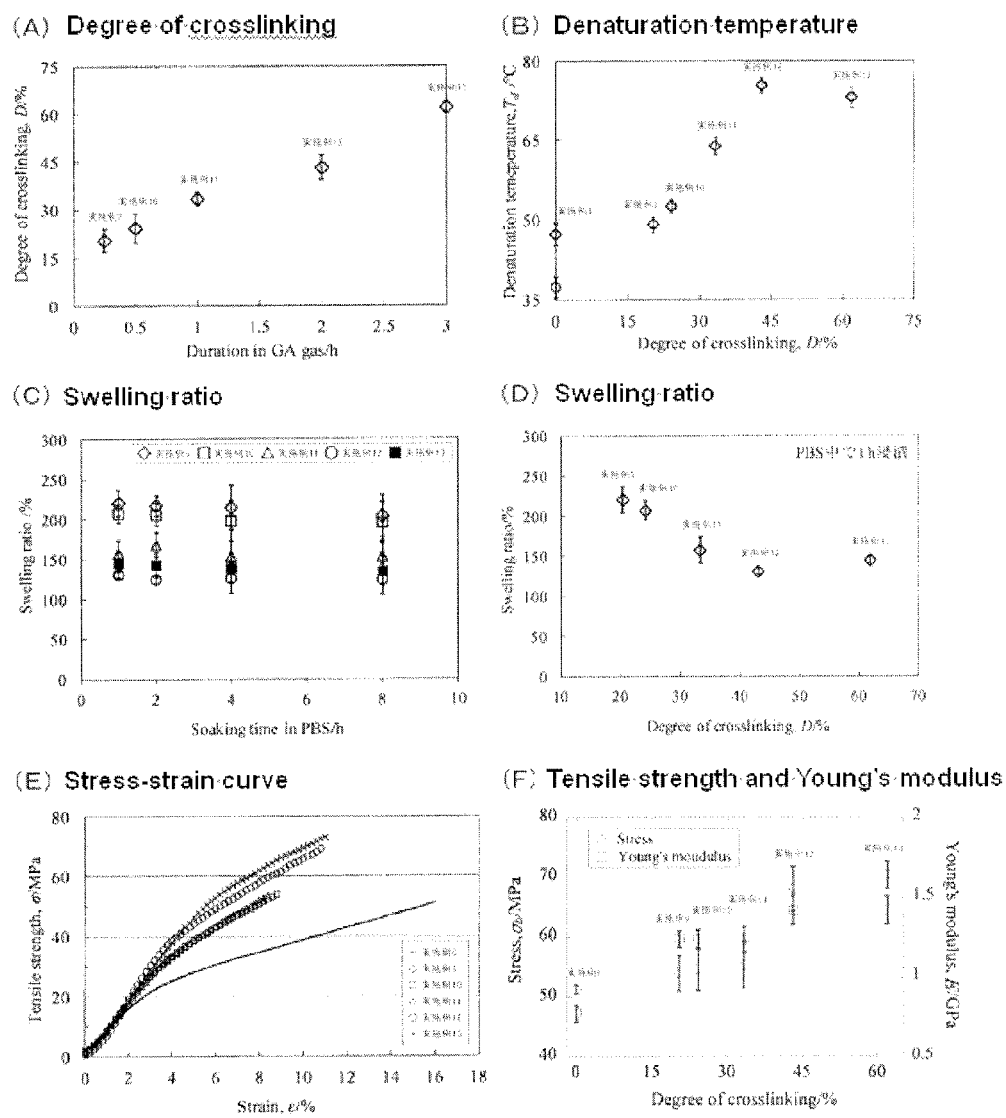
FIG. 8 is a set of graphs showing: a degree of cross-linking (A), denaturation temperatures (B), swelling ratio (C and D), stress-strain curves (E), and tensile strength and Young's modulus (F), of the collagen fiber membrane cross-linked by glutaraldehyde vapor.

The relationship between the treatment time of cross-linking and the degree of cross-linking is shown in FIG. 8A. The degree of cross-linking was increased, in a linear manner, in proportion to the treatment time of cross-linking as shown in FIG. 8A.

<<Measurement of Denaturation Temperature>>

The denaturation temperature of the resulting cross-linked and high-strength collagen fiber membrane was measured. The denaturation temperature was measured by differential scanning calorimetry.

Five to 6 mg of a specimen was weighed from each collagen fiber membrane prepared in Examples 9 to 13. After immersing in Dulbecco's PBS for 24 hours, an excess fluid was wiped off from the specimen. Then, the specimen was sealed in an aluminum pan and the differential scanning calorimetry was carried out. A temperature range from −10° C. to 100° C. was scanned at a rate of temperature increase of 3° C./min. The relationship between the degree of cross-linking and the denaturation temperature is shown in FIG. 8B. The denaturation temperature of a collagen molecule dispersed in hydrochloric acid solution (lower point at 0 of the degree of cross-linking) is approximately 36° C., and the denaturation temperature of a collagen fiber membrane, wherein the collagen fibrils were formed and prepared in Example 8 (upper point at 0 of degree of cross-linking), was increased by approximately 10° C. As shown in FIG. 8B, the denaturation temperature was correlated in a linear manner with the degree of cross-linking. Further, the denaturation temperature of collagen having 60% or more of a degree of cross-linking is similar to one of collagen having 45% of a degree of cross-linking.

<<Swelling Ratio>>

The swelling ratio of the resulting cross-linked and high-strength collagen fiber membrane was measured. The swelling ratio measurement was carried out as follows.

Each collagen fiber membrane prepared in Examples 9 to 13 was immersed in Dulbecco's PBS for 1 hour, 2 hours, 4 hours, or 8 hours at 38° C. Then, the collagen fiber membrane was collected from Dulbecco's PBS, and an excess PBS was wiped off with a paper towel (Kimwipe) from the membrane. The swelling ratio was measured by weight changes before and after treatment. The swelling ratio (%) was calculated using the following formula:

$(W_{PBS}-W_{DRY})/W_{DRY}\times 100$

Variation of the swelling ratio according to the immersion time is shown in FIG. 8C. The swelling ratios after 1 hour of immersion were not varied. Further, the degree of cross-linking was negatively-correlated to the swelling ratios after a 1 hour immersion (FIG. 8D). However, the swelling ratio of collagen having 60% of the degree of cross-linking is similar to a collagen having 45% of the degree of cross-linking.

<<Tensile Strength>>

The tensile strength and Young's modulus of the cross-linked collagen fiber membrane were measured. In the tensile strength test, the gap distance was 10 mm and the measurement was carried out by pulling the specimen at a rate of 0.5 mm/minute. As shown in FIG. 7, the specimen has a form with 10 mm×20 mm, and the central width becomes narrower, from 10 mm to 5 mm.

The stress-strain curves of collagen fiber membranes prepared in Examples 8 to 13 were shown in FIG. 8E. Further, the relationships between the degree of cross-linking and tensile strength or Young's modulus were shown in FIG. 8F. From the stress-strain curves, the specimen, which was not crosslinked, exhibits the highest strain. In the treatment time for 15 min to 1 hour, variations of tensile strength cannot be observed. However, the increases of tensile strength and strain were observed with the increase of the cross-linking time (2 hours or 3 hours). The reason for this is presumed to be as follows. When the treatment time of cross-linking was short, collagen molecules in collagen fibril were cross-linked by glutaraldehyde. While, when the treatment time of cross-linking had become long, the collagen fibers were cross-linked by glutaraldehyde. From the relationships between the degree of cross-linking and tensile strength or Young's modulus, it is considered that the degree of cross-linking is correlated to the physical property of the material in a linear manner.

<<Morphological Change of Collagen Fibril after Tensile Strength Test>>

The morphological change of collagen fibril in a collagen fiber membrane after a tensile strength test was analyzed with the scanning-electron microscope.

Figure 9:
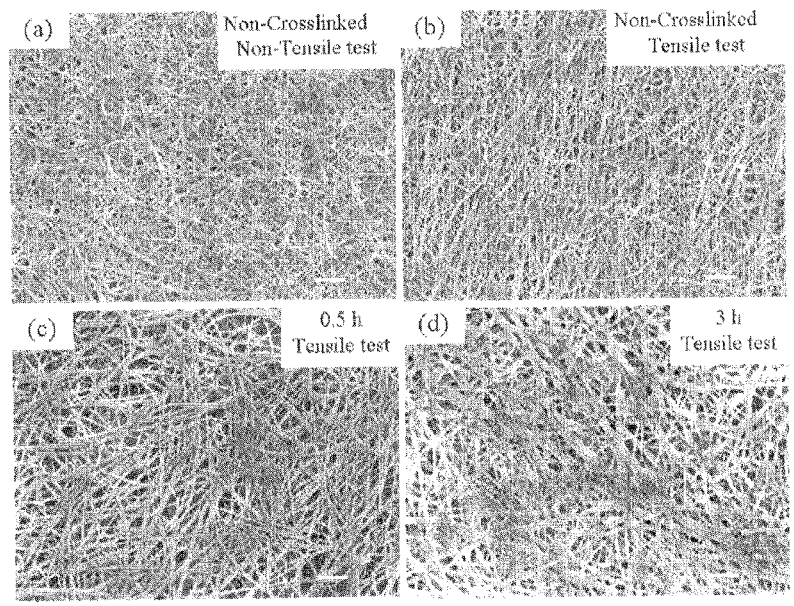
FIG. 9 is a set of paragraphs showing various fiber forms of non-cross-linked collagen fiber membranes before tensile strength test (a) and after tensile strength test (b), and collagen fiber membrane cross-linked by glutaraldehyde vapor for 30 minutes (c) and for 3 hours (d).

The collagen fiber membrane was coated with 20 nm of platinum, and observed at 5 kV of accelerating voltage. The electron micrograph is shown in FIG. 9. In the non-cross-linked collagen fiber membrane prepared in Example 8, the collagen fiber was extended in the same direction along the pulled direction by the tensile strength test, and thus it was observed that the direction of collagen fibers became constant (FIG. 9b). In the collagen fiber membranes, which were cross-linked for 30 minutes (Example 10; FIG. 9c) and 3 hours (Example 13; FIG. 9d), changes in the direction of collagen fibers were not observed.

<<Cell Culture>>

In this Example, human bone-marrow-derived mesenchymal stem cells (hMSC) were cultured using the high-strength collagen fiber membrane (20 mm of diameter) which was prepared by the method in Example 7. Further, a collagen-transparent membrane was prepared by cast film process using a collagen solution containing a collagen molecule (Comparative Example 8). Then, hMSCs were cultured using the collagen transparent membrane prepared in Comparative Example 8. Furthermore, hMSCs were cultured without collagen, i.e. using a 12-well cell culture plate made of polystyrene (FALCON).

Each well of a 12-well cell culture plate made of polystyrene was set in the high-strength collagen fiber membrane of Example 7, or the collagen-transparent membrane of Comparative Example 8. Human bone-marrow-derived mesenchymal stem cells (hMSC; Lot. No. 6F3974; $1.0 \times 10^4$ cells/well) were seeded on a well containing each collagen membrane, or a well without collagen membranes. hMSCs were cultured in D-MEM (High-Glucose) containing 10% FBS, at 37° C. under 5% $CO_2$ conditions. When culturing, an osteoblast differentiation factor was not added. After one day of culturing, alkaline phosphatase activity was measured in order to examine osteoblast differentiation ability. Cells were washed with PBS(−)(pH7.4), and then collected by a cell scraper. The collected cells were suspended in 200 μL of a 100 mM Tris-HCl (pH7.5) buffer (containing 5 mM $MgCl_2$, and 0.2% Triton X-100), and sonicated. After sonication, the whole was centrifuged at 6,000 g for 10 minutes, and the supernatant was collected. Alkaline phosphatase activities of 20 μL of supernatant or diluted supernatant, which was optionally diluted with 100 mM Tris-HCl (pH7.5) buffer (containing 5 mM $MgCl_2$), were measured using LabAssay ALP (Wako).

Figure 10:
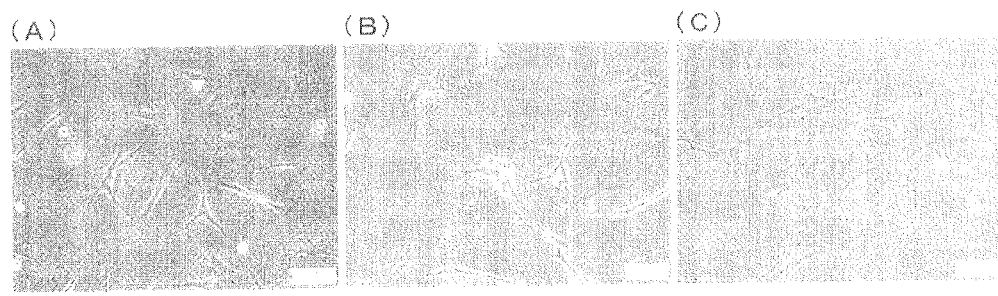

A photograph of cell morphology after culturing for 1 day is shown in FIG. 10. In all cell culture substrates, cells were extended, as shown in FIG. 10. Further, the measured results of alkaline phosphatase (ALP) activities were shown in FIG. 11. When the high-strength collagen fiber membrane was used, alkaline phosphatase activities of cells were increased, and thus hMSCs may differentiate into osteoblasts.

In the culture without a collagen membrane, osteoblasts may not be differentiated. Further, in the culture with the collagen-transparent membrane, the differentiation ability of osteoblasts was low. However, hMSCs can differentiate into osteoblasts by using the high-strength, fish-derived collagen fiber membrane.

INDUSTRIAL APPLICABILITY

The fish-derived collagen fiber membrane can be used as a cell culture substrate, a scaffold material for regenerative medicine (for example, material for tissue engineering of cartilage, bone, ligament, corneal stroma, skin, or liver), an implantation material (for example, wound dressing material, bone grafting material, hemostatic material, anti-adhesive material) or a carrier for drug delivery.

Although the present invention has been described with reference to specific embodiments, various changes and modifications obvious to those skilled in the art are possible without departing from the scope of the appended claims.

The invention claimed is:

1. A fish-derived collagen fiber membrane, characterized in that (1) a tensile strength is 30 MPa or more, (2) a density determined by the gravimetric method, is 0.4 g/cm³ or more, and (3) an average membrane thickness is 1 μm to 2 mm, and a variation in membrane thickness is plus or minus 30%, relative to the average membrane thickness.

2. The fish-derived collagen fiber membrane according to claim 1, wherein the collagen is derived from a fish scale.

3. The fish-derived collagen fiber membrane according to claim 2, wherein the collagen fiber membrane is cross-linked.

4. The fish-derived collagen fiber membrane according to claim 3, for induction of osteoblast differentiation.

5. The fish-derived collagen fiber membrane according to claim 2, for induction of osteoblast differentiation.

6. The fish-derived collagen fiber membrane according to claim 1, wherein the collagen fiber membrane is cross-linked.

7. The fish-derived collagen fiber membrane according to claim 6, for induction of osteoblast differentiation.

8. The fish-derived collagen fiber membrane according to claim 1, for induction of osteoblast differentiation.

9. A method for preparing a fish-derived collagen fiber membrane, comprising the steps of:
(1) forming a collagen fibril from a soluble collagen in a collagen solution, to obtain a collagen fiber gel of 0.3% by weight or more,
(2) removing a salt from the collagen fiber gel using a graded series of purified water and ethanol, and
(3) drying the collagen fiber gel by covering a lower surface and an upper surface of the collagen fiber gel and evaporating a solvent from a side of the collagen fiber gel,
wherein the fish-derived collagen fiber membrane is characterized in that (1) a tensile strength is 30 MPa or more, (2) a density determined by the gravimetric method, is 0.4 g/cm³ or more, and (3) an average membrane thickness is 1 μm to 2 mm, and a variation in membrane thickness is plus or minus 30%, relative to the average membrane thickness.

10. The method for preparing a fish-derived collagen fiber membrane according to claim 9, wherein the collagen is derived from a fish scale.

11. The method for preparing a fish-derived collagen fiber membrane according to claim 10, further comprising a step of cross-linking the fish-derived collagen fiber membrane.

12. The method for preparing a fish-derived collagen fiber membrane according to claim 9, further comprising a step of cross-linking the fish-derived collagen fiber membrane.

* * * * *